(12) United States Patent
Nishi et al.

(10) Patent No.: US 8,034,975 B2
(45) Date of Patent: Oct. 11, 2011

(54) METHOD OF MANUFACTURING SUCCINIC ACID AND AMMONIUM SUCCINATE SOLUTIONS

(75) Inventors: Kiyohiko Nishi, Saga (JP); Hiroshi Kaneko, Saga (JP); Hirofumi Tasaki, Saga (JP); Masaki Koga, Saga (JP); Tetsuo Tanegawa, Saga (JP); Seisaku Furuya, Saga (JP); Kenji Fujiwara, Saga (JP); Takeru Sato, Saga (JP)

(73) Assignee: Ajinomoto Co., Inc., Tokyo (JP)

( * ) Notice: Subject to any disclaimer, the term of this patent is extended or adjusted under 35 U.S.C. 154(b) by 167 days.

(21) Appl. No.: 12/620,747

(22) Filed: Nov. 18, 2009

(65) Prior Publication Data
US 2010/0094051 A1    Apr. 15, 2010

Related U.S. Application Data

(63) Continuation of application No. PCT/JP2008/058569, filed on May 8, 2008.

(30) Foreign Application Priority Data

May 18, 2007  (JP) ................................. 2007-132917

(51) Int. Cl.
*C07C 55/00*    (2006.01)
(52) U.S. Cl. ........................................ 562/593; 562/590
(58) Field of Classification Search .................. None
See application file for complete search history.

(56) References Cited

U.S. PATENT DOCUMENTS

| | | | | |
|---|---|---|---|---|
| 5,143,833 | A | * | 9/1992 | Datta ............................. 435/145 |
| 5,168,055 | A | * | 12/1992 | Datta et al. .................... 435/145 |
| 5,958,744 | A | * | 9/1999 | Berglund et al. ............. 435/145 |
| 7,189,543 | B2 | | 3/2007 | Nishi et al. |
| 2006/0276674 | A1 | * | 12/2006 | Kushiku et al. ............... 562/562 |
| 2007/0015264 | A1 | * | 1/2007 | Isotani et al. ................. 435/136 |

FOREIGN PATENT DOCUMENTS

| | | |
|---|---|---|
| EP | 0249773 | 12/1987 |
| EP | 0405707 | 1/1991 |
| EP | 1686183 | 8/2006 |
| JP | 02-283289 | 11/1990 |
| JP | 03-030685 | 2/1991 |

(Continued)

OTHER PUBLICATIONS

International Search Report for PCT Patent App. No. PCT/JP2008/058569 (Aug. 12, 2008).

(Continued)

*Primary Examiner* — Karl J Puttlitz
(74) *Attorney, Agent, or Firm* — Shell Guest Cermak; Cermak Nakajima LLP (57) ABSTRACT

The present invention provides a method of manufacturing a highly pure ammonium succinate solution including the steps of (A) producing calcium succinate trihydrate by crystallization fermentation of a microorganism; (B) converting calcium succinate trihydrate to calcium succinate monohydrate by transition crystallization; (C) separating the calcium succinate monohydrate crystals; (D) substituting the calcium salt in the calcium succinate monohydrate with ammonium salt resulting in an ammonium succinate solution; and (E) removing the solid calcium carbonate from the ammonium succinate solution.

6 Claims, 1 Drawing Sheet

Comparison of Succinic Acid Crystals
Magnification of microscope was 500 times.
A) Calcium succinate trihydrate crystals obtained by using high purity raw materials.
B) Calcium succinate crystals accumulated in fermentation solution.

FOREIGN PATENT DOCUMENTS

| | | |
|---|---|---|
| JP | 11-092502 | 4/1999 |
| JP | 2004-196768 | 7/2004 |
| JP | 2005-139137 | 6/2005 |
| JP | 2005-295998 | 10/2005 |
| WO | WO99/09196 | 2/1999 |
| WO | WO2005/021770 | 3/2005 |
| WO | WO2005/026349 | 3/2005 |

OTHER PUBLICATIONS

International Preliminary Examination Report for PCT Patent App. No. PCT/JP2008/058569 (Jan. 21, 2010).

Supplementary European Search Report for EP Patent App. No. 08752455.9 (May 11, 2011).

* cited by examiner

[Fig. 1]

Comparison of Succinic Acid Crystals
Magnification of microscope was 500 times.
A) Calcium succinate trihydrate crystals obtained by using high purity raw materials.
B) Calcium succinate crystals accumulated in fermentation solution.

[Fig. 2]

A) Calcium succinate trihydrate crystals accumulated in fermentation solution

B) Calcium succinate monohydrate crystals produced by the transition of A)

METHOD OF MANUFACTURING SUCCINIC ACID AND AMMONIUM SUCCINATE SOLUTIONS

This application is a continuation under 35 U.S.C. §120 of PCT Patent Application No. PCT/JP2008/058569, filed May 8, 2008, which claims priority under 35 U.S.C. §119 to Japanese Patent Application No. 2007-132917, filed on May 18, 2007, which are incorporated in their entireties by reference.

BACKGROUND OF THE INVENTION

1. Technical Field

This invention relates to a method of manufacturing succinic acid and ammonium succinate solutions using fermentation.

2. Background Art

Succinic acid and its derivatives are widely used as raw materials in the manufacture of foods, perfumes, cosmetics, and medicines. Furthermore, succinic acid has been recently used in monomers of biodegradable plastics. The succinic acid used in these applications is produced by a petrochemical method. Alternatively, the production of succinic acid by fermentation has been recently investigated using carbohydrates of plant origin as raw materials.

When producing succinic acid by a fermentation method, the culture pH should generally be maintained at around neutral, so that microorganisms can exhibit the necessary and sufficient activities. As a neutralizing agent, calcium hydroxide, sodium hydroxide, magnesium hydroxide, ammonia, calcium carbonate, sodium carbonate, magnesium carbonate and ammonium carbonate, etc. can be used. As a result, the corresponding succinic acid salts can accumulate in the culture solution.

Among the succinic acid salts, it is known that calcium succinate has a low solubility, and can precipitate as crystals into the culture solution (JP62-294090A). Usually, the culture solution contains a mixture of raw materials for fermentation, such as sugars, various additives, such as nutrients for the chosen microorganism, and by-products produced by the metabolism of microorganism, etc. Because calcium succinate is easily removed from the culture solution due to precipitation of the crystals, purification of succinic acid can be simple. Furthermore, since further purification methods to isolate the succinate crystals, such as concentration, are unnecessary, the precipitation of calcium salt is advantageous from the viewpoint of energy consumption.

A typical method of separating succinic acid from succinate salts is to lower the pH until free succinic acid is generated by adding an acid, such as sulfuric acid. For calcium succinate, a method of obtaining succinic acid by using sulfuric acid is known (JP3-30685A). However, this method has limitations since sufficient amounts of calcium sulfate do not precipitate as a by-product.

To separate succinic acid from succinates without using acid, electrodialysis has been proposed (JP2-283289A). Since bases which separate from succinic acid during the purification process are reused as neutralizing agents in fermentation, by-products are not produced. However, this method is limited to the succinic acid salts with monovalent bases, such as sodium succinate and ammonium succinate. For calcium salt, this method is unsuitable due to the precipitation and build-up of debris on the membrane used for filtration. For these reasons, studies using calcium compounds as neutralizing agents have not been conducted in recent years.

Alternatively, when succinic acid is obtained from ammonium succinate using sulfuric acid, ammonium sulfate is produced as a by-product. A method of preventing the generation by-product salts was finally proposed by pyrolyzing the produced by-product ammonium sulfate at 300° to produce ammonium hydrogen sulfate and ammonia, and then reusing them in the process (JP2001-514900A).

In addition, a method of using acetic acid has also been proposed for obtaining succinic acid from ammonium succinate (JP2004-196768A). Generation of by-product salts is prevented by pyrolyzing the ammonium sulfate produced as a by-product, resulting in production of acetic acid and ammonia, and then reusing them in the process. As mentioned above, ammonium succinate can be used as a starting material in the purification process of succinic acid.

Ammonium succinate can accumulate in the culture solution by using ammonia, or the like, as a neutralizing agent in the fermentation process. However, it is known that ammonia is not the most efficient neutralizing agent for producing succinic acid, and from the viewpoint of productivity and yield during fermentation, magnesium compounds can be effective (WO2005/026349A).

Various purification methods are applicable to the magnesium salt, which results in a favorable form of this salt during the fermentation process. Furthermore, and in view of the methods disclosed in JP2001-514900A and JP2004-196768A which do not generate salt by-products, a method in which the salt is substituted was proposed to convert the ammonium salt into a more favorable form (JP2005-295998A). The magnesium compound produced by substituting the salt is reused as a neutralizing agent in the fermentation process. Magnesium succinate which is produced in the fermentation process is dissolved in the culture solution, and usually does not precipitate as crystals. Therefore, the salt substitution step is carried out by adding ammonium carbonate or the like to the culture solution. As a result, the mixture in the culture solution, other than magnesium succinate, is carried into the ammonium succinate solution which is the starting material for the purification process. Therefore, an additional step is necessary to remove the complicated mixture before or after the salt substitution step.

An efficient method of manufacturing ammonium succinate solution by fermentation has not been previously described.

SUMMARY OF THE INVENTION

Calcium succinate can be efficiently produced by adding a calcium compound, which acts a neutralizing agent, during the fermentation process. Furthermore, a highly pure ammonium succinate solution can be manufactured by isolating calcium succinate, and then substituting the salt using an ammonium compound.

It is an aspect of the present invention to provide a method of manufacturing a highly pure ammonium succinate solution comprising (A) producing calcium succinate trihydrate by crystallization fermentation of a microorganism; (B) converting calcium succinate trihydrate to calcium succinate monohydrate by transition crystallization; (C) separating the calcium succinate monohydrate crystals; (D) substituting the calcium salt in the calcium succinate monohydrate with ammonium salt resulting in an ammonium succinate solution; and (E) removing the solid calcium carbonate from the ammonium succinate solution.

It is a further aspect of the present invention to provide the method as described above, wherein a calcium compound selected from the group consisting of calcium hydroxide, calcium oxide, calcium hydrogen carbonate, calcium carbonate, and combinations thereof is used in step (A).

It is a further aspect of the present invention to provide the method as described above, wherein step (B) occurs at a temperature of 80° or higher.

It is a further aspect of the present invention to provide the method as described above, wherein ammonium carbonate or ammonia, and carbon dioxide gas, are present in step (D).

It is a further aspect of the present invention to provide the method as described above, wherein a concentration of 5% by weight or more of succinic acid is present in step (D).

It is a further aspect of the present invention to provide a method of manufacturing succinic acid comprising (A) producing the ammonium succinate solution according to the method described above, and (B) producing succinic acid from the ammonium succinate solution produced in step (A).

From the ammonium succinate solution, succinic acid can be manufactured by a known method (see JP2001-514900A and JP2004-196768A, etc.). In addition, calcium carbonate produced by the salt substitution can be reused as a fermentation neutralizing agent. Alternatively, it is also possible to neutralize by calcium hydroxide which is produced by calcining calcium carbonate by a known method (Ed. by Sekko Sekkai Gakkai, "Sekko Sekkai Handbook (Gypsum-Line Handbook)", pp 126-144, Gihodo Shuppan, 1972) and hydrating the produced calcium oxide. Furthermore, carbon dioxide generated by the calcination can be used effectively in the fermentation and salt substitution steps.

According to the description herein, ammonium succinate solution can be manufactured efficiently and simply, and from the ammonium succinate solution, succinic acid can be manufactured by a known method which produces only reusable by-products.

DETAILED DESCRIPTION OF THE EXEMPLARY EMBODIMENTS

A multi-step method is described, and the steps will be described herein.

A) Fermentation Step

As a first step, succinic acid is produced in a culture solution by fermentation. Manufacturing succinic acid by fermentation has been previously described and used, and typically is conducted by culturing a strain capable of producing succinic acid while neutralizing with a calcium compound to produce succinic acid. Although the microorganisms which can be used for the fermentation are not particularly limited, aerobic bacteria or facultative anaerobic bacteria, specifically a coryneform bacterium, *Bacillus* bacterium, *Rhizobium* bacterium, or *Escherichia* bacterium can be used. As the coryneform bacterium, microorganisms belonging to the genus *Corynebacterium*, *Brevibacterium*, or *Arthrobacter* can be included. Microorganisms belonging to *Corynebacterium glutamicum*, *Brevibacterium flavum*, *Brevibacterium ammoniagenes*, or *Brevibacterium lactofermentum* can be used.

In particular, *Brevibacterium flavum* MJ-233 (FERM BP-1497), MJ-233 AB-41 (FERM BP-1498) which is a mutant of the MJ-233, *Brevibacterium ammoniagenes* ATCC 6872, *Corynebacterium glutamicum* ATCC 31831, ATCC 13032 and *Brevibacterium lactofermentum* ATCC 13869, and the like, can be used. Since *Brevibacterium flavum* is now sometimes classified as *Corynebacterium glutamicum* (Lielbl, W., Ehrmann, M., Ludwig, W. and Schleifer, K. H., International Journal of Systematic Bacteriology, 1991, vol. 41, p 255-260), *Brevibacterium flavum* MJ-233 strain and its mutant MJ-233 AB-41 strain can be referred to as *Corynebacterium glutamicum* MJ-233 strain and MJ-233 AB-41 strain.

Strains which can be used include the above strains, and also include strains derived from the above strains via mutation or gene manipulation. For example, *Corynebacterium glutamicum* MJ 233/Δldh is a mutant strain which lacks lactate dehydrogenase and can be used. Mutant strains can be derived by the method described in WO 2005/021770. Furthermore, the fermentation process may be divided into a bacterial cell culture step and a succinic acid fermentation step for the purpose of improving productivity.

a) Bacterial Cell Culture Step

The culture of any of the above-described microorganisms can be conducted under aerobic atmospheric conditions with aeration and stirring.

Hereupon, the phrase "under aerobic atmospheric conditions" can mean conditions under which bacterial cells multiply while consuming oxygen. Although the concentration of dissolved oxygen is not particularly limited, for efficient multiplication, it can be 4% or more, in another example 20% or more, so to achieve saturation of the dissolved oxygen.

A typical nutrient medium can be used as the culture medium for cultivation, such as one that contains a carbon source, a nitrogen source, inorganic salts, and optional other organic minor nutrients, such as amino acids and vitamins. Either a synthetic medium or a natural medium can be used. The carbon source and nitrogen source can be able to be used by the chosen strain.

As the carbon source, sugars, such as glucose, glycerol, fructose, sucrose, maltose, mannose, galactose, starch hydrolyzate, and molasses, and moreover, organic acids, such as acetic acid and citric acid can be used singly or in combination with other carbon sources.

As the nitrogen sources, ammonia, ammonium salts, such as ammonium sulfate, ammonium carbonate, ammonium chloride, ammonium phosphates and ammonium acetate, and nitrates can be used.

As the organic minor nutrients, amino acids, vitamins, fatty acids, nucleic acids, and moreover, materials containing these, such as peptone, casamino acids, yeast extracts, and soybean protein hydrolyzates can be used. When an auxotrophic mutant requiring amino acids, or the like, for its metabolism or growth is used, such required nutrients can be added to the culture.

As the inorganic salts, phosphates, magnesium salts, calcium salts, iron salts, manganese salts, and the like can be used.

The form or type of cultivation is not particularly limited. However, in order to obtain a greater concentration of bacterial cells, a fed batch culture and continuous culture where the substrate is sequentially added can be used, and higher bacterial cell yields can be realized.

The culture temperature and pH are not particularly limited, so long as the chosen microorganism can multiply. Typically, the temperature is in the range of 20° to 40°, and the pH is in the range of 6.0 to 8.0.

Cultivation can be carried out until the cell amount is in the range of 30 to 120 g/l, expressed as dry cell weight, for example.

b) Calcium Succinate Trihydrate Crystallization Fermentation Step

Succinic acid fermentation is carried out by reacting the bacterial cells, which have been cultured as described above, with a carbon source under anaerobic atmospheric conditions, and neutralizing the succinic acid which is produced with a calcium compound. By reacting under the appropriate conditions for the cultured bacterial cells, succinic acid can be produced and will accumulate in the culture medium while calcium succinate trihydrate will precipitate.

The phrase "under anaerobic atmospheric conditions" means that the dissolved oxygen concentration is 0.1 ppm or less, or in another example 0.01 ppm or less. In order to induce such conditions, the oxygen supply can be restricted. The oxygen supply can be restricted by reducing the aeration, limiting the stirring, and/or introducing a gas which has a reduced partial pressure of oxygen by mixing in an inert gas, such as nitrogen or carbon dioxide. The anaerobic atmosphere can be made completely anaerobic by removing the oxygen entirely. To completely remove the oxygen, aeration can be stopped, or only an inert gas can be introduced, or the like.

The quantity of the cultured bacterial cells to be used for the reaction is not particularly limited; however, it can be 1 to 120 g/l, or in another example, 10 to 80 g/l. The bacterial cell culture solution can be used as is. Alternatively, materials in the culture solution can be removed by a known method, such as centrifugation, prior to the reaction.

The carbon source for succinic acid fermentation is not particularly limited, as long as it can be digested by the microorganism chosen to produce succinic acid, and carbon sources similar to the bacterial cell culture can be used.

The timing of the addition of the carbon source is also not particularly limited, and for example, the total amount of the carbon source necessary to produce the desired amount of succinic acid can be added before the start of the reaction. Alternatively, the carbon source can be added a little bit at a time to coincide with the consumption of the carbon source as the reaction proceeds. Furthermore, the total amount of carbon source can be added successively.

The calcium compounds which can be used to neutralize succinic acid include calcium carbonate ($CaCO_3$)), calcium oxide (CaO), calcium hydroxide ($Ca(OH)_2$), calcium hydrogen carbonate ($Ca(HCO_3)_2$), and the like, and although not particularly limited, calcium hydroxide can be beneficial because the pH can be easily controlled. In addition, two or more of these calcium compounds can be used in combination.

The form of the calcium compound is not particularly limited, but should be within a range capable of controlling the pH to an appropriate value. For example, the calcium compound can be added as a slurry, or it can be in powder form.

The reaction temperature and pH are not particularly limited, but should be within a range capable of producing succinic acid, and in general, the temperature can be in the range of 20° to 40°, and the pH can be in the range of 4.0 to 8.0.

The culture medium that can be used for the reaction is not particularly limited, and can be within a range where it will not inhibit the succinic acid producing reaction. For example, it can contain only a carbon source. In addition, additives other than the carbon source can be added. For example, phosphoric acid compounds, such as phosphoric acid, can be added to accelerate the reaction. The timing of the addition of the additives, other than the carbon source, is not particularly limited, and they can be added all at once, for example, at the start of the reaction. Alternatively, they can be added successively as the reaction proceeds.

Moreover, carbonate ion, bicarbonate ion, or carbon dioxide gas can be incorporated into the culture medium. The method by which these are added is not particularly limited, and for example, carbon dioxide can be added using aeration. If aerated, the concentration of carbon dioxide gas can be 5% or more. However, when calcium carbonate is used as a neutralizing agent, carbonate ion and bicarbonate ion can also be added.

The type of fermenter to be used for the reaction is not particularly limited, and for example, a mechanical stirring type fermenter commonly used for amino acid fermentation, and the like, can be used. A bubble tower type culture vessel (see, e.g. JP11-092502A) can also be used.

As the reaction proceeds, calcium succinate trihydrate crystals precipitate. The reaction continues until the desired amount of calcium succinate is produced and has accumulated in the reaction solution. In general, the reaction continues until calcium succinate has accumulated in an amount of 30 g/l or more, or in another example, 50 g/l or more, expressed as the weight of succinic acid. The reaction time is usually 10 to 48 hours. The reaction can continue and the deposited crystals can be removed from the fermenter.

(B) Transition Step

Figure 1:
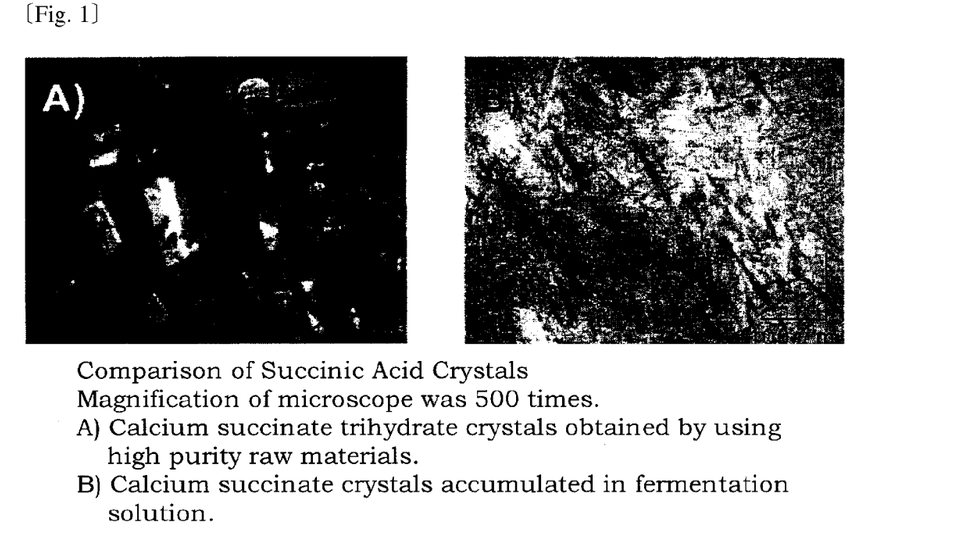
FIG. 1 is photographs that show the comparison of crystal forms between calcium succinate trihydrate (A) obtained by using a high purity raw material (reagent level) and calcium succinate trihydrate (B) which has accumulated in a fermentation solution.

The calcium succinate trihydrate crystals which precipitate in the reaction solution can be collected by centrifugation or filtration. However, as shown in FIG. 1, the calcium succinate trihydrate crystals produced by fermentation are considerably finer, for example, needle crystals, as compared with the calcium succinate trihydrate crystals produced under high purity conditions, for example, by reacting guaranteed grade succinic acid with calcium hydroxide manufactured by Wako Junyaku Co., Ltd. By converting the crystals to calcium succinate monohydrate crystals, which are easier to separate, the separation of the calcium succinate crystals is easier, particularly because the reaction solution contains a mixture of materials, such as bacterial cells and reaction by-products.

The transition reaction is carried out by heating the reaction solution. The transition point from the trihydrate to the monohydrate is at around 60° for pure reagents, and higher than that, and up to around 80° for culture solution. Optimum conditions can be different depending on the composition of the reaction solution, and in general, can be conducted by heating to 80° or more. The reaction time depends on the temperature, and in the case of a reaction temperature of 80°, it is usually for 2 to 24 hours. These conditions can be easily determined by a person skilled in the art by observing the crystal state.

Figure 2:
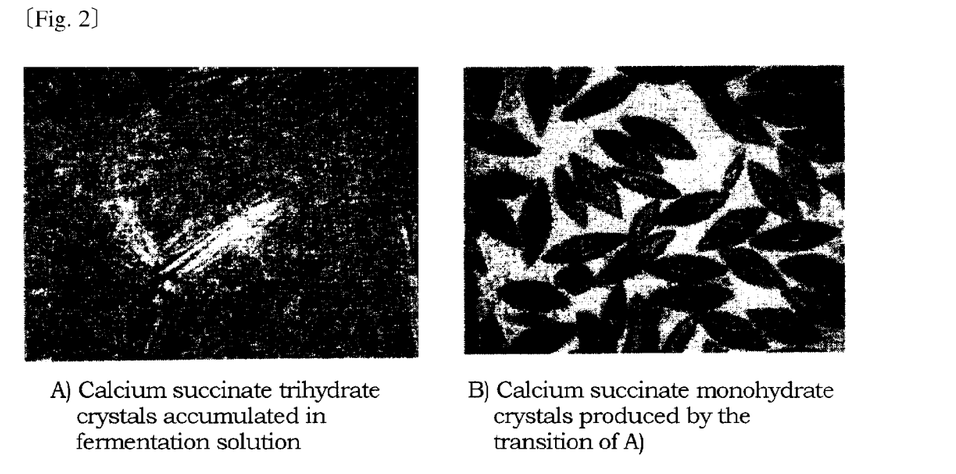
FIG. 2 is photographs that show the comparison of crystal forms between calcium succinate trihydrate (A) which has accumulated in a fermentation solution and calcium succinate monohydrate (B) obtained by the transition of (A).

As shown in FIG. 2, the crystal form varies from needle shaped crystals (calcium succinate trihydrate) to ellipsoid shaped crystals (calcium succinate monohydrate) in the reaction solution. The monohydrate crystals are relatively stable, and when temperature lowers, a return to the trihydrate form does not occur easily.

(C) Crystal Separation Step

In this step, calcium succinate monohydrate crystals are separated, for example, around 60° from the reaction solution in which the transition crystallization has occurred. The reaction solution contains bacterial cells, reaction by-products, and the like in addition to the calcium succinate monohydrate crystals. The method of separating calcium succinate monohydrate crystals is not particularly limited, but an efficient separation method can utilize the difference in specific gravity.

To separate the monohydrate crystals, a screw decanter, a super decanter, and the like can be used.

The separated calcium succinate monohydrate crystals are then used in the next step. Prior to the next step, the crystals can be made into a slurry again to remove bacterial cells and impurities, and then washed. Water can be used for washing. However, when a solution of calcium succinate, preferably a saturated solution, is used for washing, the loss of succinic acid can be prevented. By separating the slurry thus obtained, calcium succinate monohydrate crystals can be obtained again.

Since 10 to 20 g/l of succinic acid is dissolved in the reaction solution, when the calcium succinate monohydrate precipitates out of the solution, the dissolved succinic acid remains in solution. To increase the recovery of calcium succinate monohydrate crystals, for example, the mother liquor can be further concentrated which will increase the amount of crystals precipitating out of the solution. In addition, the amount of precipitated crystals can be increased by concentrating the reaction solution prior to the separation step. Alternatively, the mother liquor can be returned to the fermentation step, and thereby, the whole calcium succinate monohydrate crystals can be recovered.

(D) Salt Substitution Step

This step effects the change from calcium succinate monohydrate to ammonium succinate, and produces and precipitates the calcium carbonate. With this reaction, succinic acid produced as calcium salt in the fermentation step can be converted to an ammonium salt solution.

By reacting calcium succinate monohydrate and ammonium carbonate by mixing, the salt substitution occurs, wherein the calcium is replaced with ammonium in the ammonium succinate solution. Alternatively, the salt substitution reaction may be carried out by adding ammonia and carbon dioxide gas. These conditions can be appropriately varied by the person skilled in the art.

The succinic acid concentration in the reaction solution can be within a range so that crystals of ammonium succinate produced by the salt substitution do not precipitate, and in general, can be 5 to 40% by weight of succinic acid. The succinic acid concentration can be adjusted easily by controlling the volume of additional water during the salt substitution reaction.

When using ammonium carbonate for the salt substitution, in general, the carbonate can be added in an amount of 0.5 to 5 times, or in another example 0.5 to 2 times, relative to the moles of calcium in the reaction solution. The "calcium in the reaction solution" can mean the total amount of the calcium present in calcium succinate and calcium compounds. The calcium in the reaction solution is precipitated as calcium carbonate by reacting with carbonate ions.

When the reaction is carried with ammonia and carbon dioxide gas, the carbon dioxide gas is added in a volume of 0.5 to 5 times, or in another example, 0.5 to 2 times, relative to the moles of calcium in the reaction solution. The ammonia can be added either as aqueous ammonia or ammonia gas. The additional amount of ammonia can be chosen so that the pH of the reaction solution is within a range to induce precipitation of calcium carbonate. This pH range can be 5.0 to 9.0, or in another example 6.0 to 8.0.

The reaction solution can be stirred during the reaction. The reaction time is not particularly limited, and the reaction is generally completed between 0.5 and 5 hours.

(E) Solid-Liquid Separation Step to Remove Calcium Carbonate

In this step, calcium carbonate can be removed from the slurry mixture of the ammonium succinate solution and the precipitated calcium carbonate, which was produced in the salt substitution step, to obtain an ammonium succinate solution.

The separation of calcium carbonate may be carried out by either filtration or specific gravity separation.

According to this step, a high purity ammonium succinate solution can be obtained where the combination of succinic acid and ammonia make up 90% or more of the total solid component.

The separated calcium carbonate can be reused in the fermentation process. Alternatively, calcium hydroxide, which is a neutralizing agent that can be used in the fermentation process, can be produced by known calcination and hydration methods.

Moreover, the carbon dioxide gas generated by the calcination can be recovered and reused in the fermentation step or the salt substitution step.

Using the ammonium succinate solution, succinic acid can be produced by a known method. The method of producing succinic acid is not particularly limited, and for example, a method of using acetic acid (JP2004-196768A) can be employed.

EXAMPLES

The invention will be explained in detail hereinafter with reference to the following non-limiting Examples.

Example 1

A method is described with the following steps: the crystallization fermentation step for manufacturing calcium succinate trihydrate using the strain *Corynebacterium glutamicum* MJ233/Δldh and neutralizing with calcium hydroxide, the transition step for producing calcium succinate monohydrate by heating the culture solution, the crystal separation step for separating crystals from the reaction solution, the salt substitution step for substituting the calcium salt with the ammonium salt, and the solid-liquid separation step to obtain calcium carbonate that precipitates from the ammonium salt solution.

Step A: Fermentation Step

Seed Culture:

A 100 ml culture medium containing 30 g/l glucose, 0.4 g/l magnesium sulfate 7 hydrates, 1.0 g/l potassium dihydrogen phosphate, 12 g/l urea, 0.5 g/l DL-methionine, 10 mg/l ferrous sulfate 7 hydrates, 10 mg/l manganese sulfate 5 hydrates, 0.3 mg/l D-biotin, 0.2 mg/l thiamin hydrochloride, 28.6 ml/l soybean protein hydrolyzate (containing 35 g/l total nitrogen) and 10 g/l yeast extract, was placed in a 50 ml Sakaguchi flask, and sterilized by heating at 120° for 20 minutes. After cooling to room temperature, the strain *Corynebacterium glutamicum* MJ233/Δldh was seeded, and cultured with shaking at 31.5° for 22 hours.

Bacterial Cell Culture:

1500 ml of a culture medium containing 20 g/l glucose, 2.0 g/l magnesium chloride 7 hydrates, 2.0 g/l orthophosphoric acid, 1.0 g/l citric acid monohydrate, 14.3 ml/l soybean protein hydrolyzate (containing 35 g/l total nitrogen), 0.8 g/l ammonium chloride, 1.0 g/l DL-methionine, 200 mg/l manganese sulfate 5 hydrates, 3 mg/l D-biotin, 1 mg/l thiamin hydrochloride, and 0.25 ml/l anti-foaming agent was prepared, and sterilized at 120° for 20 minutes. After cooling to room temperature, the culture medium was placed in a 5 l reaction vessel, and 9 ml of the above seed culture solution was added, and maintained at 31.5°. The culture was conducted with stirring and aerating at 1.5 l/min and the pH was adjusted to 6.6 with ammonia gas. After culturing for 8.0 hours, a previously sterilized glucose solution (500 g/l) was continuously added at a rate of 25 ml/hour until the culture was finished. When 340 ml of the glucose solution had been introduced, the culture was finished, and a bacterial cell culture solution containing about 50 g/l bacterial cells was obtained.

A culture medium containing 100 g/l glucose, 2.0 g/l orthophosphoric acid and 0.05 ml/l anti-foaming agent (the above concentrations are after seeding the bacterial cell culture solution) was prepared, and placed in a 5 l reaction vessel. After sterilizing at 120° for 20 minutes, the culture medium was maintained at 34°, and 840 ml of the above bacterial cell culture solution was added. The total volume was 2.11 liters, and a culture was carried out with stirring. In the stirring culture, a mixed gas having an air:nitrogen gas:carbon dioxide gas ratio of 10:70:20 was aerated at 210 ml/min., and the pH was maintained at neutral around pH6.6 by adding a calcium hydroxide slurry (260 g/l).

The reaction was continued for 24 hours. As a result, the glucose that was introduced was completely consumed, and 2.89 kg (2.65 l) of the reaction solution with 57.0 g/l of accumulated succinic acid was obtained. The yield of the conversion of glucose to succinic acid was 72%. The succinic acid concentration of supernatant of the reaction solution was 13.3 g/l, and therefore, it was calculated that 77% of succinic acid in the reaction solution was present in the form of the calcium salt. The culture was similarly conducted using 4 vessels, and 589 g succinic acid was obtained in the calcium salt form from 11.17 kg (10.75 l) of the total reaction solution.

Step B: Transition Step 9.70 kg of the above reaction solution was placed in a stainless steal vessel having a total volume of 30 l, and heated to 80° in a water bath. This temperature was maintained for about 18 hours with stirring. A change in crystal form was observed, and as a result of x-ray diffraction, it was found that calcium succinate trihydrate crystals were converted to calcium succinate monohydrate crystals. Before and after the transition reaction, water was evaporated by heating, but the quantity of succinic acid was not varied. 9.28 kg of the reaction solution was obtained, and 571 g succinic acid was obtained. The succinic acid concentration in the supernatant of the reaction solution was 15.4 g/l, and the solubility of succinic acid was not greatly varied before and after the transition reaction.

Step C: Crystal Separation Step

After cooling 9.28 kg of the reaction solution in which the transition had been achieved to about 60°, the solid-liquid separation was carried out by a screw decanter. The decanter was manufactured by Tomoe Industries Co., Ltd., and set at 1334 rpm for the inner cylinder and 3000 rpm for the outer cylinder. The reaction solution was introduced at a flow rate of 30 l/hour. The separation was finished after about 20 minutes, and the portions that adhered on the cylinders were combined with the separated cake. The separated mother liquor was 8.07 kg and the cake was 0.99 kg. The results before and after the separation are shown in Table 1. 67.2% of succinic acid in the reaction solution was recovered. 38.4% of the separated cake was succinic acid. The cake was evaporated to dryness, and the weight was measured. As a result, it was found that succinic acid and calcium made up 81.9% of the total solid matter. It was confirmed that 70% or more of the introduced bacterial cells were removed into the separated mother liquor.

TABLE 1

|  | Before Separation | Separated Cake | Separated Mother Liquor |
|---|---|---|---|
| Weight (kg) | 9.28 | 0.99 | 8.07 |
| Succinic Acid (wt %) | 6.16 | 38.4 | 1.22 |
| Acetic Acid (wt %) | 0.73 | 0.72 | 0.75 |
| Ca Conc. (wt %) | 2.73 | 13.96 | 0.99 |
| Succinic Acid (g) | 572 | 380 | 98 |
| Ca/Succinic Acid (mol/mol) | 1.28 | 1.05 | 2.37 |
| Total Solid Matter (g) | 1239 | 634 | 468 |
| Succinic Acid/Total Solid Matter (wt %) | 46.1 | 60.1 | 21.0 |
| Bacterial Cell Quantity (g) | 89.9 | 24.8 | 62.9 |

Step D: Salt Substitution Step 630 g (containing 242 g succinic acid) of the cake recovered in the above separation step was used for the salt substitution step. The cake was placed in a 5,000 ml beaker, and 1.58 kg water was added. The cake was suspended by stirring at an ordinary temperature to form a slurry solution. Subsequently, 175 g ammonium carbonate (guaranteed grade, Wako Junyaku Co., Ltd.), which was 0.8 time in moles relative to the calcium in the slurry, was introduced, and allowed to react with stirring at an ordinary temperature for 2 hours. 2.24 kg of the salt substitution reaction solution was obtained which was in a slurry state.

Step E: Solid-Liquid Separation Step 2.24 kg of the slurry solution obtained in the above salt substitution reaction was separated into the filtrate and precipitate by a Nutsche funnel filtration. Finally, 1.82 kg of the solution and 0.42 kg of the precipitates were obtained. The molar ratio of the succinic acid in the solution was 1.92 to ammonia and 0.13 to calcium, respectively. It was found that 91% of calcium was removed as precipitates by the salt substitution reaction, and an ammonium succinate solution was obtained. Calcium in the removed precipitates was 32.2% of the total solid matter, and succinic acid was less than 8.0%.

The analyzed results of the solution obtained in the salt substitution and solid-liquid separation step are shown in Table 2. The succinic acid made up 72.7% of the total solid matter. It was found that the succinic acid and ammonia made up 93.1% of the total solid matter, and a high purity ammonium succinate solution was obtained.

TABLE 2

|  | Solution after Substitution • Separation |
|---|---|
| Weight (kg) | 1.82 |
| Succinic Acid (wt %) | 10.1 |
| Acetic Acid (wt %) | 0.23 |
| Ca Conc. (wt %) | 0.44 |
| NH3 Conc. (wt %) | 2.83 |
| Ca/Succinic Acid (mol/mol) | 0.13 |
| NH3/Succinic Acid (mol/mol) | 1.92 |
| Succinic Acid/Total Solid Matter (wt %) | 72.7 |
| Succinic acid + NH3/Total Solid Matter (wt %) | 93.1 |

Example 2

The influence of the quantity of ammonium carbonate in the salt substitution step was examined. To 80 g calcium succinate monohydrate (Junsei Kagaku Co., Ltd., guaranteed grade), 188 g water was added to form a slurry solution with a 20% by weight succinic acid concentration. To this solution, varying quantities of ammonium carbonate were added. After reacting for 2 hours with stirring, ammonium succinate solutions were obtained by centrifugation to remove precipitates.

The analyzed results of the obtained ammonium salt solutions are shown in Table 3. It indicates that 97.7% of calcium was removed from the solution by adding equimolar ammonium carbonate with the calcium in the slurry, and the succinic acid was recovered as an ammonium salt solution. It was found that almost 100% of the calcium was removed by adding a slight excess of ammonium carbonate, i.e, 1.5 times the quantity of the calcium, and succinic acid was completely converted to ammonium salt.

TABLE 3

| Experiment No. | 1 | 2 | 3 | 4 |
|---|---|---|---|---|
| Ammonium Carbonate (mol/mol Charged Ca) | 1 | 1.5 | 2 | 4 |
| Reaction Solution pH | 7.29 | 7.81 | 8.26 | 8.23 |
| Succinic Acid (wt %) | 22.0 | 23.0 | 21.2 | 16.7 |
| NH3 Conc. (wt %) | 5.6 | 6.5 | 6.8 | 11.4 |
| Ca Conc. (wt %) | 0.21 | 0.01 | 0.00 | 0.01 |
| NH3/Succinic Acid (mol/mol) | 1.66 | 1.97 | 2.23 | 4.48 |
| Ca/Succinic Acid (mol/mol) | 0.03 | 0.01 | 0.00 | 0.02 |
| Ca Removal Rate (1 − Solution Ca Quantity/Charged Ca Quantity) × 100 | 97.7 | 99.9 | 100.0 | 99.8 |

Example 3

Using the calcium succinate monohydrate crystals obtained from the reaction solution similar to Example 1, experiments were carried out similar to Example 2 with varying quantities of ammonium carbonate. To 50 g of calcium succinate crystals (succinic acid: 19.2 g), 153 g water was added, and suspended with stirring to form a 10 wt. % succinic acid slurry. Ammonium carbonate was added, and allowed to react at an ordinary temperature for 2 hours with stirring. After the reaction, precipitates were removed by centrifugation to obtain an ammonium succinate solution.

The results of the obtained ammonium salt solutions are shown in Table 4. They indicate that 92% or more of the calcium in the slurry can be removed as precipitates by adding ammonium carbonate in a quantity 0.5 time or more relative to the moles of the calcium in the slurry. It also indicates that 99% or more of the calcium in the slurry can be removed as precipitates by adding ammonium carbonate in a quantity 1.5 times or more relative to the moles.

TABLE 4

| Experiment No. | 1 | 2 | 3 | 4 |
|---|---|---|---|---|
| Ammonium Carbonate (mol/mol Charged Ca) | 0.5 | 0.9 | 1.5 | 1.8 |
| Reaction Solution pH | 7.31 | 7.50 | 8.40 | 8.40 |
| Succinic Acid (wt %) | 8.86 | 9.08 | 9.48 | 9.32 |
| NH3 Conc. (wt %) | 1.47 | 2.51 | 3.73 | 4.61 |
| Ca Conc. (wt %) | 0.33 | 0.31 | 0.01 | 0.03 |
| NH3/Succinic Acid (mol/mol) | 1.79 | 1.95 | 3.19 | 3.26 |
| Ca/Succinic Acid (mol/mol) | 0.17 | 0.10 | 0.00 | 0.01 |
| Ca Removal Rate (1 − Solution Ca Quantity/Charged Ca Quantity) × 100 | 92.0 | 92.5 | 99.6 | 99.3 |

Example 4

Experiments were carried out wherein the salt substitution was conducted as to crystals obtained similar to Example 1, wherein the concentration of charging slurry in the salt substitution step was varied. The quantity of ammonium carbonate that was added was equimolar with the calcium in the slurry. After the salt substitution reaction, precipitates were removed by centrifugation to obtain an ammonium succinate solution.

The results of the obtained ammonium salt solutions are shown in Table 5. In all of the Experiments Nos. 1, 2, 3, it was indicated that 99% or more of the charged calcium can be removed as precipitates by conducting salt exchange. Moreover, in Experiment No. 3, the succinic acid concentration of the solution after substitution reached 28 wt. %, and it indicates that a high concentration ammonium succinate solution can be obtained by conducting salt exchange of calcium succinate without concentration.

TABLE 5

| Experiment No. | 1 | 2 | 3 |
|---|---|---|---|
| Succinic Acid in Slurry before Salt Substitution (wt %) | 25 | 30 | 35 |
| Ammonium Carbonate (mol/mol Charged Ca) | 1.0 | 1.0 | 1.0 |
| Reaction Solution pH | 8.21 | 7.94 | 8.19 |
| Succinic Acid (wt %) | 17.5 | 23.0 | 28.4 |
| NH3 Conc. (wt %) | 8.1 | 9.6 | 10.5 |
| Ca Conc. (wt %) | 0.02 | 0.02 | 0.02 |
| NH3/Succinic Acid (mol/mol) | 2.88 | 2.59 | 2.29 |
| Ca/Succinic Acid (mol/mol) | 0.0 | 0.0 | 0.0 |
| Ca Removal Rate (1 − Solution Ca Quantity/Charged Ca Quantity) × 100 | 99.9 | 99.9 | 99.9 |

Example 5

Collection of Succinic Acid Crystals

Collection of succinic acid crystals was carried out from the ammonium succinate solution obtained in Example 1 by the acetic acid addition method (JP 2005-139137). 1.72 kg of the ammonium succinate solution was concentrated by a rotary evaporator at 70° under reduced pressure to obtain 400 g of a 38.4 wt. % succinic acid solution. The concentrated solution was taken in a beaker, and 193 g of acetic acid, which is 2.4 times mole of succinic acid, was added with stirring. Furthermore, 120 g of methanol, which was 20 wt. % against the reaction solution, was added to produce a slurry solution.

The slurry solution was filtered to obtain 113.6 g crystals. The crystals contained 61.4% succinic acid and 8.7% ammonia. The molar ratio of succinic acid and ammonia was 0.97, and it was found that mono-ammonium succinate crystals were produced.

194 g acetic acid was added to the crystals produced above, and allowed to react with stirring. The reacted slurry solution was filtered to obtain 58.2 g crystals. The succinic acid content, acetic acid content, and ammonia content of the crystals were 61.1%, 35.6%, and 1.2%, respectively.

The crystals obtained above were washed with 5 times volume of water followed by filtering, and then dried. The purity of succinic acid of the crystals thus obtained was 96.7%. The ratio by weight of ammonia and calcium to succinic acid were 0.03% and 0.04%, respectively, and it was confirmed that succinic acid crystals were produced.

Comparative Example 1

As a comparison, neutralization with ammonia was carried out in the fermentation step. An ammonium succinate solution was obtained by removing bacterial cells from the reaction solution.

Fermentation Step

*Corynebacterium glutamicum* MJ233/Δldh strain was used. The bacterial cell culture and succinic acid fermentation were carried out similar to Example 1, wherein neutralization of the reaction solution was conducted using 120 g/l aqueous ammonia instead of calcium hydroxide.

In a 24 hour culture, about 30 g/l glucose remained, and therefore, the reaction was continued up to 48 hours. As a result, glucose was consumed completely to obtain 2.34 kg (2.18 l) of a culture solution containing 32.2 g/l succinic acid. The yield of conversion from glucose to succinic acid was 33%.

Bacterial Cell Removal Step

Bacterial cells were removed from the culture solution obtained in the above fermentation step by centrifugation to obtain an ammonium succinate solution. The succinic acid concentration was 3.17 wt. %, and the molar ratio of ammonia and succinic acid was 2.08. The solution was dried, and the amount of succinic acid in the total solid matter was measured and found to be 44.2%. The amount of succinic acid+ammonia present in the total solid matter was 57.5%.

Comparative Example 2

As a comparison, neutralization with magnesium was carried out. Bacterial cells were removed from the reaction solution to obtain a magnesium salt solution, and the salt substitution was conducted by ammonium carbonate to obtain an ammonium succinate solution.

Fermentation Step

*Corynebacterium glutamicum* MJ233/Δldh strain was used. The bacterial cell culture and succinic acid fermentation were carried out similar to Example 1 wherein neutralization of the reaction solution was conducted, but using 205 g/l magnesium hydroxide slurry instead of calcium hydroxide.

In a 24 hour culture, about 30 g/l glucose remained, and therefore, the reaction was continued up to 48 hours. Nevertheless, glucose still remained in a concentration of about 10 g/l. 2.57 kg (2.40 l) of a culture solution containing 41.4 g/l of succinic acid was obtained. The yield of conversion from consumed glucose to succinic acid was 56%.

Bacterial Cell Removal Step

Bacterial cells were removed from the culture solution obtained in the above fermentation step by centrifugation to obtain a magnesium succinate solution. The succinic acid concentration of the solution was 4.52 wt. %, and the magnesium concentration was 0.8 wt. %.

Salt Substitution Step

To 417 g of the magnesium succinate solution obtained by the removal of bacterial cells, 16.3 g ammonium carbonate was introduced, and allowed to react with stirring. As a result of continuing the reaction for 2 hours, the solution became a slurry.

Solid-Liquid Separation Step

The slurry reaction solution obtained above was centrifuged to separate precipitates, and an ammonium succinate solution was obtained. The succinic acid concentration of the solution was 4.52 wt. %. The molar ratio of ammonia and succinic acid was 1.57. The solution was dried, and the amount of succinic acid present in the total solid matter was measured and found to be 54.0%. The amount of succinic acid+ammonia present in the total solid matter was 66.2%.

The fermentation results in Example 1, Comparative Example 1, and Comparative Example 2 are compared in Table 6. It can be seen that good fermentation results can be obtained by neutralization with calcium.

TABLE 6

|  | Example 1 | Comparative Example 1 | Comparative Example 2 |
|---|---|---|---|
| Succinic Acid (g/l) | 57.0 | 32.2 | 41.4 |
| Culture Time (hr) | 24 | 48 | 48 |
| Conversion Yield of Glucose (wt %) | 72 | 33 | 56 |

The analyzed results of the ammonium salt solutions obtained in Example 1, Comparative Example 1, and Comparative Example 2 are summarized in Table 7. It can be seen that the purity of the ammonium succinate solution produced by the calcium salt fermentation through the salt substitution is very high.

TABLE 7

|  | Example 1 | Comparative Example 1 | Comparative Example 2 |
|---|---|---|---|
| Succinic Acid (wt %) | 10.1 | 3.17 | 4.52 |
| Acetic Acid (wt %) | 0.23 | 0.82 | 0.84 |
| NH3 Conc. (wt %) | 2.83 | 0.95 | 1.02 |
| Ca Conc. (wt %) | 0.44 | 0.00 | 0.00 |
| Mg Conc. (wt %) | 0.00 | 0.00 | 0.80 |
| NH3/Succinic Acid (mol/mol) | 1.92 | 2.08 | 1.57 |
| Succinic Acid/Total Solid Matter (wt %) | 72.7 | 44.2 | 54.0 |
| Succinic acid + NH3/Total Solid Matter (wt %) | 93.1 | 57.5 | 66.2 |

INDUSTRIAL APPLICABILITY

An efficient and simple production method of ammonium succinate solutions is described, and from the ammonium succinate solution, succinic acid can be manufactured by a known method. Only reusable by-products are produced in the manufacture of succinic acid.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method of manufacturing a highly pure ammonium succinate solution comprising:
   (A) producing calcium succinate trihydrate by crystallization fermentation of a microorganism;
   (B) converting calcium succinate trihydrate to calcium succinate monohydrate by transition crystallization;
   (C) separating the calcium succinate monohydrate crystals;
   (D) substituting the calcium salt in the calcium succinate monohydrate with ammonium salt resulting in an ammonium succinate solution; and
   (E) removing the solid calcium carbonate from the ammonium succinate solution.

2. The method of manufacturing the ammonium succinate solution as set forth in claim 1, wherein a calcium compound selected from a group consisting of calcium hydroxide, calcium oxide, calcium hydrogen carbonate, calcium carbonate, and combinations thereof is used in step (A).

3. The method of manufacturing the ammonium succinate solution as set forth in claim 1, wherein step (B) occurs at a temperature of 80° C. or higher.

4. The method of manufacturing the ammonium succinate solution as set forth in claim 1, wherein ammonium carbonate or ammonia, and carbon dioxide gas are present in step (D).

5. The method of manufacturing the ammonium succinate solution as set forth in claim 1, wherein a concentration of 5% by weight or more of succinic acid is present in step (D).

6. A method of manufacturing succinic acid comprising:

(A) producing the ammonium succinate solution according to the method as set forth in claim 1, and (B) producing succinic acid from the ammonium succinate solution produced in step (A).

* * * * *